United States Patent
Mochizuki et al.

(10) Patent No.: US 9,623,166 B2
(45) Date of Patent: Apr. 18, 2017

(54) MIXING APPARATUS (71) Applicant: Nikkiso Company Limited, Tokyo (JP)

(72) Inventors: Hiroaki Mochizuki, Shizuoka (JP); Harutoshi Okabe, Shizuoka (JP)

(73) Assignee: NIKKISO COMPANY LIMITED, Tokyo (JP)

( * ) Notice: Subject to any disclaimer, the term of this patent is extended or adjusted under 35 U.S.C. 154(b) by 119 days.

(21) Appl. No.: 14/096,467

(22) Filed: Dec. 4, 2013

(65) Prior Publication Data
US 2014/0098627 A1 Apr. 10, 2014

Related U.S. Application Data (63) Continuation of application No. PCT/JP2012/064555, filed on Jun. 6, 2012.

(30) Foreign Application Priority Data

Jun. 8, 2011 (JP) .................................. 2011-128553

(51) Int. Cl.
*A61M 1/36* (2006.01)
*A61M 1/16* (2006.01)
(Continued)

(52) U.S. Cl.
CPC .............. *A61M 1/36* (2013.01); *A61M 1/169* (2013.01); *A61M 1/1656* (2013.01); *B01F 3/088* (2013.01);
(Continued)

(58) Field of Classification Search
CPC ......... A61M 1/169; A61M 1/16; B01F 3/088; B01D 2321/40
(Continued)

(56) References Cited

U.S. PATENT DOCUMENTS 3,992,301 A * 11/1976 Shippey ................ B01D 61/30
210/140
4,153,554 A * 5/1979 von der Heide ........ A61M 1/16
210/135
(Continued)

FOREIGN PATENT DOCUMENTS

GB 2137070 A 10/1984
JP 63-38466 A 2/1988
(Continued)

OTHER PUBLICATIONS

Supplementary European Search Report for Application No. PCT/JP2012064555 dated Feb. 9, 2015.

*Primary Examiner* — Tony G Soohoo
*Assistant Examiner* — Elizabeth Insler
(74) *Attorney, Agent, or Firm* — The Dobrusin Law Firm, P.C.

(57) ABSTRACT

A mixing apparatus which can reliably prevent an auxiliary liquid from being unintentionally mixed into a main unit even when a failure occurs in a switching device, and which can prevent the switching device or an auxiliary flow route from being damaged even when a pressurizing device malfunctions due to the failure. The mixing apparatus includes a pipe circulating dilution water; a pipe circulating a disinfecting solution; a pressurizing pump circulating the disinfecting solution in the pipe toward the pipe; and a check valve capable of optionally turning on and off the pipe. The mixing apparatus further includes a discharge flow route which consists of a flow route branched from between the check valve and the pressurizing pump in the pipe, and which can discharge the dilution water or the disinfecting solution; and an electromagnetic valve which can control the flow route between the check valve and the pressurizing pump in the pipe to have a pressure lower than that of the pipe when not mixing the disinfecting solution with the dilution water.

15 Claims, 6 Drawing Sheets

(51) Int. Cl.
*B01F 3/08* (2006.01)
*B01F 5/04* (2006.01)
*B01F 13/04* (2006.01)
*B01F 15/00* (2006.01)

(52) U.S. Cl.
CPC ............ *B01F 5/0471* (2013.01); *B01F 13/04* (2013.01); *B01F 15/00025* (2013.01); *A61M 1/1666* (2014.02)

(58) Field of Classification Search
USPC ........................................................ 210/636
See application file for complete search history.

(56) References Cited

U.S. PATENT DOCUMENTS

| | | | |
|---|---|---|---|
| 4,683,053 A * | 7/1987 | Polaschegg | A61M 1/169 210/321.6 |
| 5,603,902 A * | 2/1997 | Maltais | A61M 1/168 134/166 C |
| 2004/0016346 A1* | 1/2004 | Deubel et al. | 99/275 |
| 2011/0268611 A1* | 11/2011 | Akahori | B01F 3/088 422/68.1 |

FOREIGN PATENT DOCUMENTS

| | | |
|---|---|---|
| JP | 2003-260131 A | 9/2003 |
| JP | 2008-023324 A | 2/2008 |
| JP | 2008-023325 A | 2/2008 |
| WO | 99/41003 A1 | 8/1999 |

* cited by examiner

MIXING APPARATUS

FIELD

The present disclosure relates to a mixing apparatus that performs pressure injection of an auxiliary liquid on a main unit through an auxiliary flow route by turning on a switching device and operating a pressurizing device when mixing the auxiliary liquid with a main liquid, and that turns off the switching device and stops the pressurizing device when not mixing the auxiliary liquid with the main liquid.

BACKGROUND

Dialysis treatment is performed by extracorporeally circulating blood of a patient in a blood circuit and by removing blood waste materials in the blood through a dialyzer connected to the blood circuit. A dialysate prepared to have desired concentration by diluting an undiluted dialysate with a diluent is supplied to the dialyzer. For example, a dialysis system called a central system type includes not only a monitoring device for performing dialysis treatment on the patient by using the dialyzer, but also a water treatment device which can produce clean water (diluting water or washing water), a dissolving device which can produce the undiluted dialysate, and a dialysate supplying device which can produce the dialysate and supply the dialysate to the monitoring device.

Then, the individual devices involved in the dialysis system include pipes for circulating the dialysate, the undiluted dialysate and the clean water. In general, during a predetermined period of time when treatment is not performed, a disinfecting process is performed in order to disinfect the pipes. For example, as a technology which can disinfect the pipes of a dialysate supplying device, there is provided a mixing apparatus in which a flow route (hereinafter, referred to as a "main unit") for circulating water (hereinafter, referred to as a "main liquid") from a water supply source is connected to a tip of a flow route (hereinafter, referred to as an "auxiliary flow route") which can circulate a disinfecting solution (hereinafter, referred to as an "auxiliary liquid"), and in which an electromagnetic valve (hereinafter, referred to as a "switching device") and a pump (hereinafter, referred to as a "pressurizing device") are provided near a merging portion of the main unit in the auxiliary flow route (refer to PTL 1).

Then, whereas when the disinfecting is not performed (treatment is performed), the switching device is turned off and the pressurizing device is stopped, when the disinfecting is performed on the pipes, the switching device is turned on and the pressurizing device is operated. In this manner, the disinfecting process is performed by injecting the auxiliary liquid to the main unit, mixing the auxiliary liquid with the main liquid, producing the disinfecting solution having the predetermined concentration, and circulating the disinfecting solution in the pipes. Then, if the switching device is turned off, it is possible to prevent the auxiliary liquid from reaching the main unit when the disinfecting is not performed. One example of a device may be found in Japanese Unexamined Patent Application Publication No. 63-38466, the teachings of which are incorporated by reference herein for all purposes.

SUMMARY

However, in the above-described mixing apparatus in the related art, the switching device is arranged in the auxiliary flow route in which the auxiliary liquid circulates, and turning on and off of the switching device causes the auxiliary fluid to be injected into the main unit, thereby enabling the auxiliary liquid to be mixed with the main liquid. Accordingly, when a failure occurs in the switching device, there is a possibility that the auxiliary liquid may be unintentionally mixed into the main unit. In addition, when the pressurizing device malfunctions due to a failure, there is also a possibility that the switching device or the auxiliary flow route may be damaged. These problems, without being limited to the mixing apparatus in the dialysate supplying device as described in the related art, are common to other devices (without being limited to other devices configuring the dialysis system, the mixing apparatus in general in which the auxiliary liquid is injected to the main unit and mixed with the main liquid).

The present disclosure is made in view of the above circumstances, and aims to provide a mixing apparatus which can prevent an auxiliary liquid from being unintentionally mixed into a main unit even when a failure occurs in a switching device, and which can prevent the switching device or the auxiliary flow route from being damaged even when a failure occurs in a pressurizing device to cause a malfunction.

According to the disclosure herein there is provided a mixing apparatus which includes a main unit that circulates or contains a main liquid; an auxiliary flow route that circulates an auxiliary liquid and whose tip is connected to the main unit; a pressurizing device that circulates the auxiliary liquid in the auxiliary flow route toward the main unit; and a switching device that is arranged near a portion in the auxiliary flow route, which is connected to the main unit, and that can optionally turn on and off the auxiliary flow route. When mixing the auxiliary liquid with the main liquid, pressure injection of the auxiliary liquid is performed on the main unit through the auxiliary flow route by turning on the switching device and operating the pressurizing device, and when not mixing the auxiliary liquid with the main liquid, the switching device is turned off and the pressurizing device is stopped. The mixing apparatus further includes a discharge flow route that consists of a flow route branched from between the switching device in the auxiliary flow route and the pressurizing device and that can discharge the main liquid or the auxiliary liquid; and a pressure control unit that can control a flow route between the switching device and the pressurizing device in the auxiliary flow route to have a pressure lower than that of the main unit, when not mixing the auxiliary liquid with the main liquid.

According to the disclosure described herein, the mixing apparatus described herein, when mixing the auxiliary liquid with the main liquid, the pressure control unit can control the flow route between the switching device and the pressurizing device in the auxiliary flow route to have a pressure equal to or greater than a pressure of the main unit.

According to the disclosure described herein, and the mixing apparatus described in the disclosure herein, the pressure control unit consists of a switching valve which is connected to the discharge flow route whose tip is exposed to air.

According to the disclosure described herein, and the mixing apparatus described in the disclosure herein, the switching valve consists of an electromagnetic valve which can turn on and off the flow route at optional times or a relief valve which can optionally set a relief pressure.

According to the disclosure described in herein, and the mixing apparatus described in in the disclosure herein, the switching valve consists of the electromagnetic valve which can be normally turned on and can be turned off by way of electric conduction at optional times. When mixing the auxiliary liquid with the main liquid, the electric conduction is performed on the electromagnetic valve and the pressurizing device, and when not mixing the auxiliary liquid with the main liquid, the electric conduction to the electromagnetic valve and the pressurizing device is stopped.

According to the disclosure described herein, and the mixing apparatus described in the disclosure herein, the switching device consists of a back pressure valve connected to the auxiliary flow route or a check valve, allows liquid circulation toward the main unit, and regulates the liquid circulation toward an opposite direction thereof.

According to the disclosure described herein, and the mixing apparatus described in the disclosure herein, the switching device and the pressure control unit are formed from a three-way valve arranged in a merging portion with the discharge flow route in the auxiliary flow route. When mixing the auxiliary liquid with the main liquid, the flow route from the pressurizing device in the auxiliary flow route toward the main unit is turned on and the flow route toward the discharge flow route is turned off, and when not mixing the auxiliary liquid with the main liquid, the flow route from the pressurizing device in the auxiliary flow route toward the main unit is turned off and the flow route toward the discharge flow route is turned on.

According to the disclosure described herein, and the mixing apparatus described in the disclosure herein, a main liquid detection device which detects the main liquid is arranged in the discharge flow route.

According to the disclosure described herein, and the mixing apparatus described in the disclosure herein, a liquid flow rate detection device which detects a liquid flow rate is arranged in the discharge flow route.

According to the disclosure described herein, and the mixing apparatus described in the disclosure herein, an auxiliary liquid detection device which detects the auxiliary liquid is arranged in the main unit.

According to the disclosure described herein, and the mixing apparatus described in the disclosure herein, after mixing the auxiliary liquid with the main liquid, the pressure control unit controls the flow route between the switching device and the pressurizing device in the auxiliary flow route to have a pressure lower than that of the main unit and operates the pressurizing device so that the auxiliary liquid detection device can determine whether or not the auxiliary liquid is detected.

According to the disclosure described herein, and the mixing apparatus described in the disclosure herein, the auxiliary liquid consists of a disinfecting solution for disinfecting the main unit.

According to the disclosure described herein, and the mixing apparatus described in the disclosure herein, the main unit consists of the flow route or a containing device for circulating or containing a dialysate for purifying blood of a patient, an undiluted dialysate, or clean water for producing the dialysate or the undiluted dialysate. The main liquid consists of dilution water for diluting the disinfecting solution and producing the disinfecting solution having predetermined concentration.

According to the disclosure described herein, there are provided the discharge flow route that consists of the flow route branched from between the switching device in the auxiliary flow route and the pressurizing device and that can discharge the main liquid or the auxiliary liquid; and the pressure control unit that can control the flow route between the switching device and the pressurizing device to have the pressure lower than that of the main unit, when not mixing the auxiliary liquid with the main liquid. Therefore, it is possible to reliably prevent the auxiliary liquid from being unintentionally mixed into the main unit even when the failure occurs in the switching device, and it is possible to prevent the switching device or the auxiliary flow route from being damaged even when the pressurizing device malfunctions due to the failure.

According to the disclosure described herein, when mixing the auxiliary liquid with the main liquid, the pressure control unit can control the flow mute between the switching device and the pressurizing device in the auxiliary flow route to have a pressure equal to or greater than a pressure of the main unit. Therefore, it is possible to reliably and smoothly inject the auxiliary liquid to the main unit, and it is possible to excellently mix the auxiliary liquid with the main liquid.

According to the disclosure described herein, the pressure control unit consists of the switching valve which is connected to the discharge flow route whose tip is exposed to the air. Therefore, the pressure control unit can be simply configured. Accordingly, it is possible to more reliably prevent the auxiliary liquid from being unintentionally mixed into the main unit even when the failure occurs in the switching device, and it is possible to more reliably prevent the switching device or the auxiliary flow route from being damaged even when the pressurizing device malfunctions due to the failure.

According to the disclosure described herein, the switching valve consists of the electromagnetic valve which can turn on and off the flow route at optional times or the relief valve which can optionally set the relief pressure. Therefore, the pressure control unit can be more simply configured.

According to the disclosure described herein, when mixing the auxiliary liquid with the main liquid, the electric conduction is performed on the electromagnetic valve and the pressurizing device, and when not mixing the auxiliary liquid with the main liquid, the electric conduction to the electromagnetic valve and the pressurizing device is stopped. Therefore, it is possible to stop power supply to the electromagnetic valve and the pressurizing device when not mixing the auxiliary liquid with the main liquid, thereby enabling running cost to be saved. In addition, when the power supply to the electromagnetic valve and the pressurizing device is inadvertently stopped due to a power failure or the like, the auxiliary liquid is not in a mixed state with the main liquid (the pressurizing device is stopped and the flow route between the switching device and the pressurizing device in the auxiliary flow route has the lower pressure than the main unit). Therefore, it is possible to improve safety.

According to the disclosure described herein, the switching device consists of the back pressure valve connected to the auxiliary flow route or the check valve, allows liquid circulation toward the main unit, and regulates the liquid circulation toward an opposite direction thereof. Therefore, it is not necessary to perform the electric conduction on the switching device. Accordingly, it is possible to eliminate a need to operate the switching device in switching between when mixing the auxiliary liquid with the main liquid and when not mixing the auxiliary liquid with the main liquid.

According to the disclosure described herein, the switching device and the pressure control unit are formed from the three-way valve arranged in the merging portion with the discharge flow route in the auxiliary flow route. When mixing the auxiliary liquid with the main liquid, the flow route from the pressurizing device in the auxiliary flow route toward the main unit is turned on and the flow route toward the discharge flow route is turned off, and when not mixing the auxiliary liquid with the main liquid, the flow route from the pressurizing device in the auxiliary flow route toward the main unit is turned off and the flow route toward the discharge flow route is turned on. Therefore, as compared to a case of forming the switching device and the pressure control unit respectively, it is possible to reduce the number of parts, and it is possible to easily perform the switching operation between when mixing the auxiliary liquid with the main liquid and when not mixing the auxiliary liquid with the main liquid.

According to the disclosure described herein, the main liquid detection device which detects the main liquid is arranged in the discharge flow route. Therefore, when not mixing the auxiliary liquid with the main liquid, it is possible to detect that the main liquid leaks into the discharge flow route due to the failure in the switching device.

According to the disclosure described herein, the liquid flow rate detection device which detects the liquid flow rate is arranged in the discharge flow route. Therefore, it is possible to detect that the main liquid or the auxiliary liquid unintentionally flows in the discharge flow route due to the failure in the switching device or the pressurizing device.

According to the disclosure described herein, the auxiliary liquid detection device which detects the auxiliary liquid is arranged in the main unit. Therefore, when mixing the auxiliary liquid with the main liquid, it is possible to detect that the auxiliary liquid is normally injected, and when not mixing the auxiliary liquid with the main liquid, it is possible to detect that the auxiliary liquid reaches the main unit due to the failure in the switching device and the pressurizing device, thereby enabling the safety to be further improved.

According to the disclosure described herein, after mixing the auxiliary liquid with the main liquid, the pressure control unit controls the flow route between the switching device and the pressurizing device in the auxiliary flow route to have the pressure lower than that of the main unit and operates the pressurizing device so that the auxiliary liquid detection device can determine whether or not the auxiliary liquid is detected. Therefore, the pressure control unit can perform a self-diagnosis, thereby enabling reliability on the device to be further improved.

According to the disclosure described herein, the auxiliary liquid consists of the disinfecting solution for disinfecting the main unit. Therefore, it is possible to more smoothly mix the disinfecting solution with the main liquid during the disinfecting, and it is possible to reliably prevent the disinfecting solution from being mixed into the main liquid when the disinfecting is not performed.

According to the disclosure described herein, the main unit consists of the flow route or the containing device for circulating or containing a dialysate for purifying blood of the patient, the undiluted dialysate, or the clean water for producing the dialysate or the undiluted dialysate. The main liquid consists of dilution water for diluting the disinfecting solution and producing the disinfecting solution having predetermined concentration. Therefore, it is possible to more smoothly mix the disinfecting solution with the dilution water during the disinfecting, and it is possible to more reliably prevent the disinfecting solution from being mixed to the dialysate, the undiluted dialysate or the clean water for producing the dialysate or the undiluted dialysate.

DETAILED DESCRIPTION

Hereinafter, an embodiment of the present disclosure will be described in detail with reference to the drawings.

Figure 1:
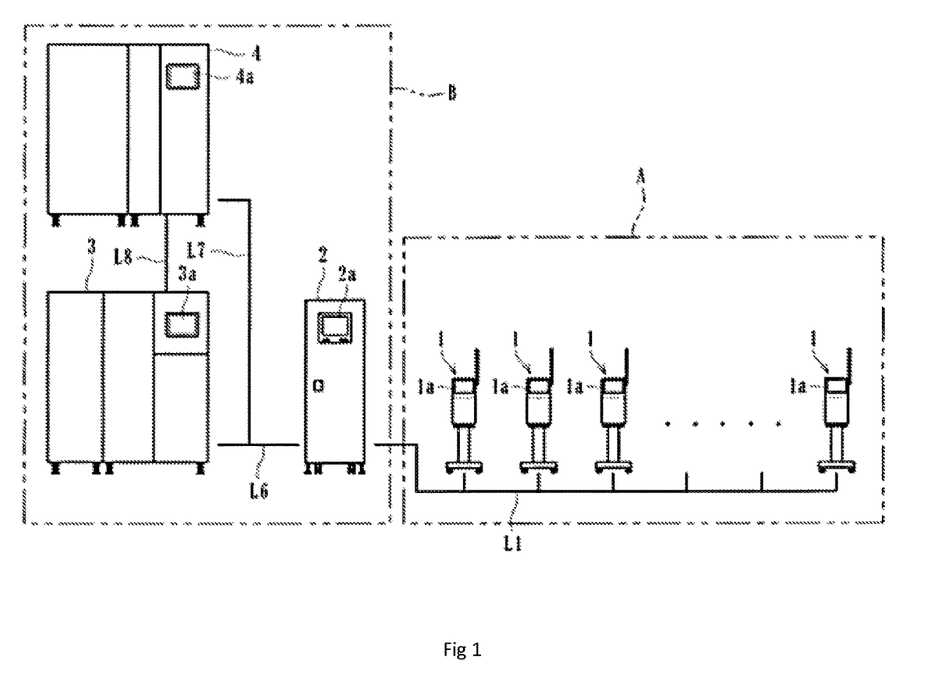
FIG. 1 is a schematic view illustrating a blood purification system to which a mixing apparatus according to an embodiment of the present disclosure is applied.

A mixing apparatus according to the present embodiment is applied to a blood purification system that produces a dialysate having predetermined concentration using an undiluted dialysate and supplies the dialysate to a plurality of dialysis monitoring devices. As illustrated in FIG. 1, the blood purification system to which the mixing apparatus is applied is mainly configured to include a plurality of monitoring devices 1 installed in a dialysis room A (treatment room) in a medical field such as hospitals; a dialysate supplying device 2 installed in a machine room B which is a place separated from the dialysis room A in the medical field: a dissolving device 3; and a water treatment device 4.

The monitoring device 1 (blood purification device) has a dialyzer 5 (blood purifier) attached thereto in order to perform a blood purification treatment (hemodialysis treatment) on a patient, and supplies the dialysate supplied from the dialysate supplying device 2 to the dialyzer 5. A plurality of monitoring devices 1 is installed at the dialysis room A. In the monitoring devices 1, touch panels 1a are arranged which can perform instruction and a predetermined display of the hemodialysis treatment or other control content (cleaning or disinfecting).

Figure 2:
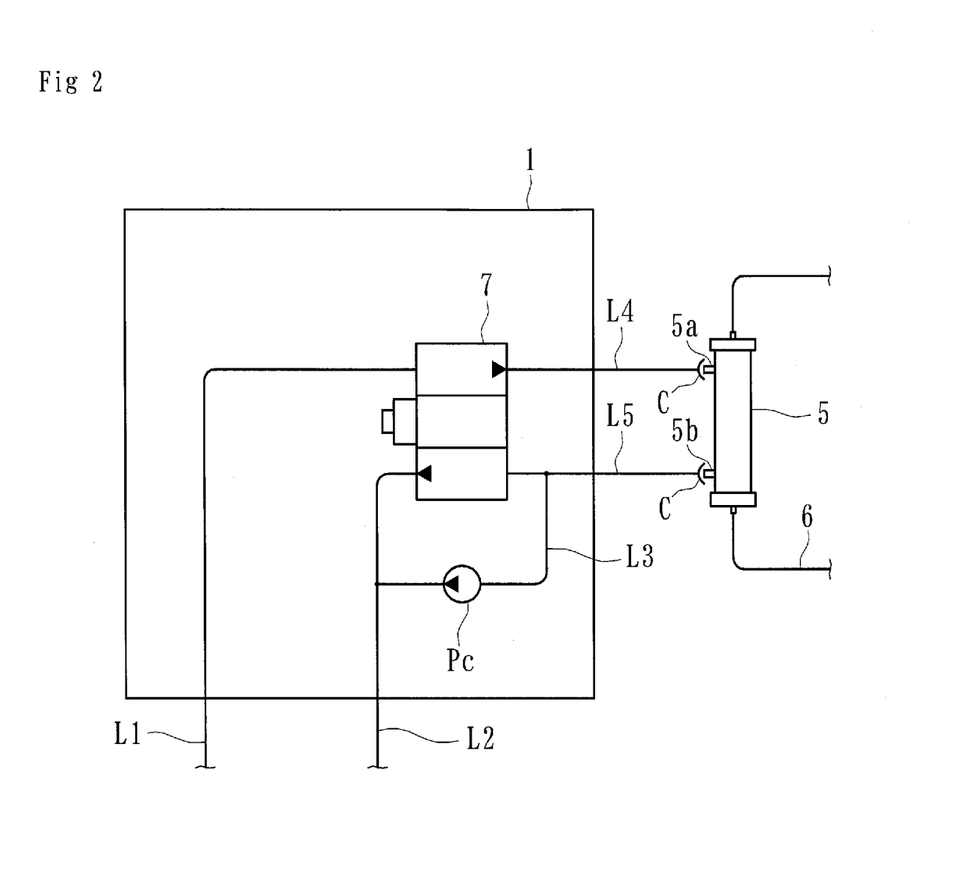
FIG. 2 is a block diagram illustrating an internal configuration of a monitoring device configuring the blood purification system, to which the monitoring device is applied.

More specifically, as illustrated in FIG. 2, a pipe L1 extending from the dialysate supplying device 2 is drawn into each of the plurality of monitoring devices 1 installed at the dialysis room A, and includes a pipe L2 which is connected to a liquid discharge device (not illustrated). A duplex pump 7 is arranged across the pipes L1 and L2. In the pipe L1 inside the monitoring device 1, a flow rate detection sensor which detects a flow rate of a liquid flowing in the pipe L1, a liquid pressure detection sensor which detects a liquid supply pressure of the liquid, and a conductivity detection sensor which detects conductivity (concentration) of the liquid are arranged (any of them is not illustrated).

In addition, a dialysate introduction line L4 communicating with the pipe L1 and a dialysate discharge line L5 communicating with the pipe L2 are extended from the duplex pump 7. A tip of the dialysate introduction line L4 can be connected to a dialysate introduction port 5a of the dialyzer 5 via a coupler C, and a tip of the dialysate discharge line L5 can be connected to a dialysate discharge port 5b of the dialyzer 5 via the coupler C. In this manner, the dialyzer 5 installed depending on each patient is attached to each monitoring device 1, and a blood circuit 6 which extracorporeally circulates blood of the patient is connected to the dialyzer 5.

A pump room of the duplex pump 7 is divided into a liquid supply side pump room connected to the pipe L1 and a discharge side pump room connected to the pipe L2 by a single plunger (not illustrated). The plunger performs reciprocation in the pump room, thereby supplying the dialysate or a cleaning solution which is supplied to the liquid supply side pump room to the dialyzer 5. Then, the dialysate inside the dialyzer 5 is sucked into the discharge side pump room. Further, a pipe L3 which bypasses the duplex pump 7 and communicates with the pipe L2 and the dialysate discharge line L5 is formed inside the monitoring device 1, and an ultrafiltration pump Pc is arranged in the middle of the pipe L3. It is possible to perform ultrafiltration on the blood of the patient which flows inside the dialyzer 5 by driving the ultrafiltration pump Pc.

Instead of the duplex pump 7, a so-called chamber type may be used. As sensors such as the flow rate detection sensor, the liquid pressure detection sensor or the conductivity detection sensor, any sensor may be arranged, or other generic sensors may be added thereto. Further, in the present embodiment, the sensors are arranged in the pipe L1, but may be arranged in the other pipe (for example, the pipe L2).

The water treatment device 4 includes a module (purifying filter) having an inherent filtration membrane therein, and obtains than water (RO water) by purifying raw water. The clean water obtained by the water treatment device 4 is used when the dialysate supplying device 2 produces the dialysate, or is used as the cleaning water for cleaning the pipes of the dialysate supplying device 2 or the monitoring devices 1. The configuration may also be made such that the water treatment device 4 is connected to a personal dialysis device (not illustrated) and supply the clean water to the personal dialysis device.

In addition, the water treatment device 4 includes a touch panel 4a which can perform instruction and a predetermined display of control content relating to the water treatment. Then, if a predetermined control signal is received from the dialysate supplying device 2, a predetermined operation (producing the clean water) is performed based on the control signal. The water treatment device 4 is connected to the dissolving device 3 and the dialysate supplying device 2 via the pipes L6 and L7, and is configured to be capable of supplying the obtained clean water to the dissolving device 3 and the dialysate supplying device 2.

The dissolving device 3, for example, receives a predetermined amount of dialysis powder drug which is injected thereto and produces the undiluted dialysate having the predetermined concentration by mixing the dialysis powder drug and the clean water supplied from the water treatment device 4. The dissolving device 3 has a touch panel 3a which can perform instruction and a predetermined display of control content relating to production of the undiluted dialysate. Then, when receiving a predetermined control signal from the dialysate supplying device 2, a predetermined operation (production of the undiluted dialysate) is performed based on the control signal. The dissolving device 3 is connected to the dialysate supplying device 2 via the pipe L6, and is configured to be capable of supplying the produced undiluted dialysate to the dialysate supplying device 2.

The dialysate supplying device 2 can produce the dialysate having predetermined concentration by using the clean water obtained from the water treatment device 4 and the undiluted dialysate produced by the dissolving device 3, and can supply the produced dialysate to each of the monitoring devices 1. That is, the dialysate supplying device 2 is connected to each of the plurality of monitoring devices 1 via the pipe L1, and is configured to be capable of supplying a desired liquid such as the dialysate, the cleaning water and the antiseptic solution to each of the monitoring devices 1 via the pipe L1. The dialysate supplying device 2 includes a touch panel 2a which can perform an instruction and a predetermined display of control content relating to the supplying of the dialysate, the cleaning or the disinfecting.

Figure 3:
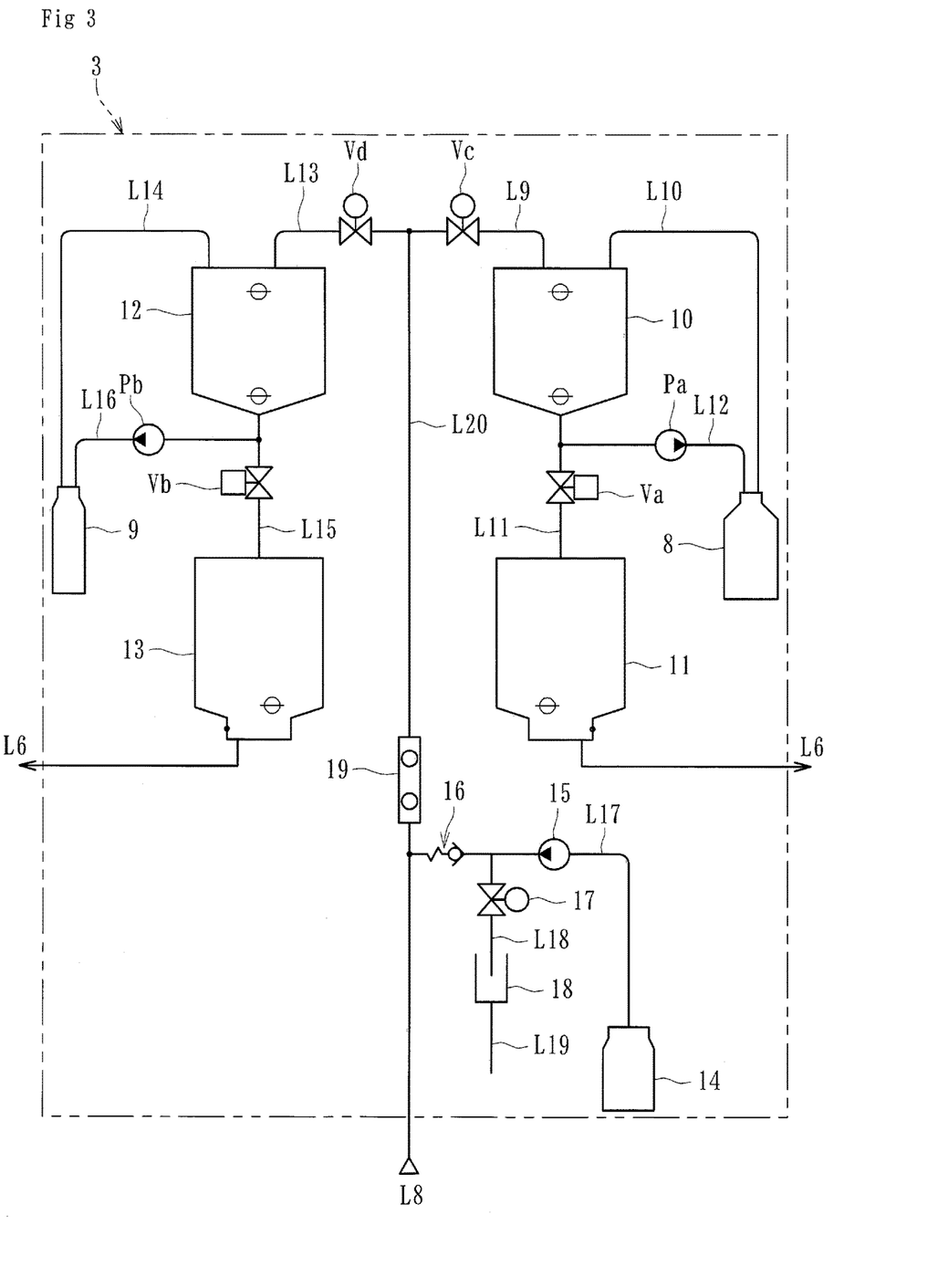
FIG. 3 is a block diagram illustrating an internal configuration of a dissolving device configuring the blood purification system, to which the dissolving device is applied.

Here, as illustrated in FIG. 3, the dissolving device 3 applied to the first embodiment has a containing device 8 which contains the dialysis powder drug having a powdered drug (drug A) excluding heavy carbon sodium and a containing device 9 which contains the dialysis powder drug having a powdered drug (drug B) consisting of sodium bicarbonate, and includes dissolving tanks 10 and 12 which produce the undiluted dialysate by dissolving the dialysis powder drug and storage tanks 11 and 13 which temporarily contain the undiluted dialysate produced in the dissolving tanks 10 and 12.

Specifically, the dissolving device 3 has a pipe L20 (main unit) connected to the water treatment device 4 via the pipe L8, and includes a pipe L9 which connects the pipe L20 to the dissolving tank 10 and a pipe L13 which connects the pipe L20 to the dissolving tank 12. Electromagnetic valves Vc and Vd are respectively arranged in the pipes L9 and L13. By selectively timing on and off the electromagnetic valves Vc and Vd, it is possible to selectively supply the clean water supplied from the water treatment device 4 to the dissolving tank 10 or the dissolving tank 12.

The dissolving tank 10 and the storage tank 11 are vertically arranged up and down, are connected to each other by a pipe L11, and a pipe L12 is branched from the middle of the pipe L11. A pump Pa is arranged in the middle of the pipe L12 and a tip portion of the pipe L12 is inserted to an opening of the containing device 8. An electromagnetic valve Va is arranged in a further downstream side (storage tank 11 side) than a branch portion with the pipe L12 in the pipe L11. In addition, a pipe L10 extends from an upper portion of the dissolving tank 10 and a tip portion of the pipe L10 is inserted to the opening of the containing device 8.

Similarly, the dissolving tank 12 and the storage tank 13 are vertically arranged up and down, are connected to each other by a pipe L15, and a pipe L16 is branched from the middle of the pipe L15. A pump Pb is arranged in the middle of the pipe L16 and a tip portion of the pipe L16 is inserted to an opening of the containing device 9. An electromagnetic valve Vb is arranged in a further downstream side (storage tank 13 side) than a branch portion with the pipe L16 in the pipe L15. In addition, a pipe L14 extends from an upper portion of the dissolving tank 12 and a tip portion of the pipe L14 is inserted to the opening of the containing device 9.

Then, in order to produce the undiluted dialysate using the dialysis powder drug consisting of the drug A, the electromagnetic valve Vc is turned on and the electromagnetic valve Vd is turned off. The clean water is supplied to the dissolving tank 10 via the pipes L20 and L9, the electromagnetic valve Va is turned off, and the pump Pa is driven. The dean water supplied to the dissolving tank 10 and the drug A inside the containing device 8 are mixed and circulated between the dissolving tank 10 and the containing device 8. Thereafter, when detecting that the liquid (undiluted dialysate) inside the dissolving tank 10 reaches the predetermined amount, the driving of the pump Pa is stopped and the electromagnetic valve Va is turned on. In this manner, the undiluted dialysate produced in the dissolving tank 10 falls in the storage tank 11 via the pipe L11 and is temporarily contained inside the storage tank 11.

On the other hand, in order to produce the undiluted dialysate using the dialysis powder drug consisting of the drug B, the electromagnetic valve Vc is turned off and the electromagnetic valve Vd is turned on. The clean water is supplied to the dissolving tank 12 via the pipes L20 and L13, the electromagnetic valve Vb is turned off, and the pump Pb is driven. The clean water supplied to the dissolving tank 12 and the drug B inside the containing device 9 are mixed and circulated between the dissolving tank 12 and the containing device 9. Thereafter, when detecting that the liquid (undiluted dialysate) inside the dissolving tank 12 reaches the predetermined amount, the driving of the pump Pb is stopped and the electromagnetic valve Vb is turned on. In this manner, the undiluted dialysate produced in the dissolving tank 12 falls in the storage tank 13 via the pipe L15 and is temporarily contained inside the storage tank 13. Then, lower portions of the storage tank 11 and the storage tank 13 are connected to the pipe L6, and the undiluted dialysate contained in the storage tanks 11 and 13 can be supplied to the dialysate supplying device 2 via the pipe L6.

Figure 4:
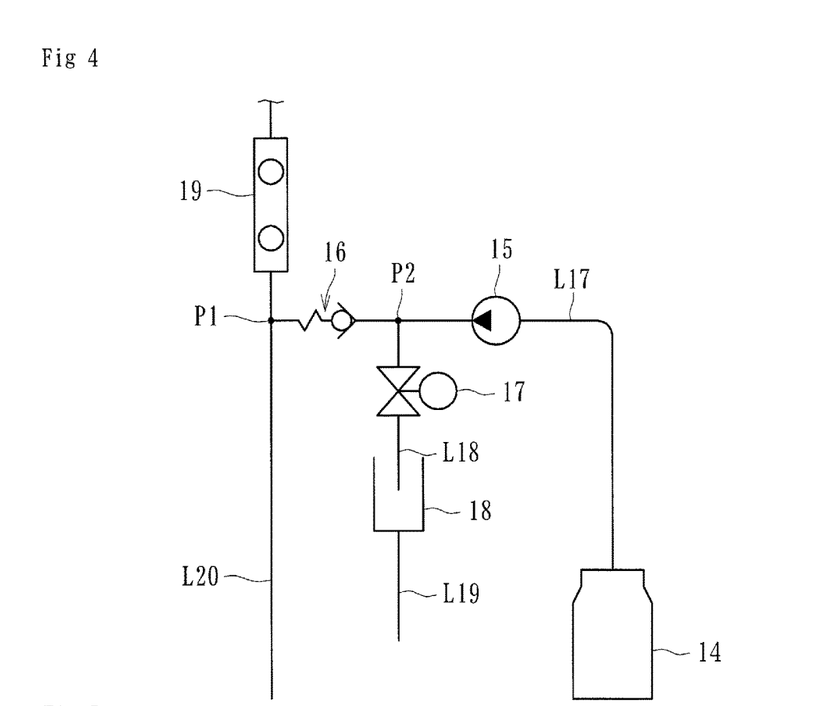
FIG. 4 is an enlarged schematic view of a mixing apparatus according to a first embodiment of the present disclosure.

Furthermore, the mixing apparatus which mixes an injected disinfecting solution with dilution water is arranged in the dissolving device 3. As illustrated in FIGS. 3 and 4, the mixing apparatus according to the first embodiment of the present disclosure includes the pipe L20 (main unit) which circulates the dilution water (main liquid: clean water): a pipe L17 (auxiliary flow route) whose base end is connected to a containing device 14 containing the disinfecting solution (auxiliary liquid) so as to circulate the disinfecting solution and whose tip is connected to a predetermined portion of the pipe L20; a pressurizing pump 15 (pressurizing device) which circulates the disinfecting solution inside the pipe L17 toward the pipe L20: and a back pressure valve 16 (switching device) which is arranged near a connecting portion P1 with the pipe L20 in the pipe L17 and can optionally turn on and off the pipe L17.

The back pressure valve 16 in the pipe L17 allows liquid (disinfecting solution) circulation toward the pipe L20, and regulates the liquid (disinfecting solution or dilution water) circulation toward an opposite direction thereof. For example, the valve is turned off by a biasing force using a spring. If the liquid pressure toward the pipe L20 which is applied to the valve reached a predetermined value, the valve is turned on against the biasing force, thereby enabling the liquid to be circulated. The disinfecting solution according to the present embodiment is sodium hypochlorite, but a disinfecting solution having other compositions may be used. In addition, instead of the back pressure valve 16, a check valve (switching device) may be used.

Then, when mixing the disinfecting solution with the dilution water (clean water circulating in the pipe L20), pressure injection of the disinfecting solution is performed on the pipe L20 through the pipe L17 by turning on the back pressure valve 16 (or the check valve) and operating the pressurizing pump 15 (in the present embodiment, the back pressure valve 16 is turned on by operating the pressurizing pump 15 and increasing a pressure of the disinfecting solution). When not mixing the disinfecting solution with the dilution water, the back pressure valve 16 (or the check valve) is turned off and the pressurizing pump 15 is stopped (in the present embodiment, the back pressure valve 16 is turned off by stopping the pressurizing pump 15 and decreasing the pressure of the disinfecting solution).

The pressurizing pump 15 according to the present embodiment consists of a diaphragm pump of an internal structure having check valves respectively in an inlet side and an outlet side. Even when an abnormality such as leakage occurs in the switching device such as the back pressure valve 16, the dilution water (main liquid) flowing in the pipe L20 can be prevented from reaching the inside of the containing device 14. Instead of the diaphragm pump, other type pumps (for example, a displacement pump having no check structure) may be used.

Here, the mixing apparatus according to the present embodiment consists of a flow route (pipe) branched from a branch portion P2 between the back pressure valve 16 and the pressurizing pump 15 in the pipe L17. The mixing apparatus includes a discharge flow route L18 which can discharge the dilution water or the disinfecting solution, and an electromagnetic valve 17 (switching valve) as a pressure control unit which can control the flow route between the back pressure valve 16 and the pressurizing pump 15 in the pipe L17 to have a pressure lower than that of the pipe L20 when not mixing the disinfecting solution with dilution water, and which can control the flow route between the back pressure valve 16 and the pressurizing pump 15 in the pipe L17 to have a higher pressure than the pipe L20 when mixing the disinfecting solution with dilution water. In the present embodiment, a tip of the discharge flow route L18 is exposed to the air, and in a lower portion of the tip, there are formed a reception member 18 which can receive the liquid (dilution water or disinfecting solution) discharged from the discharge flow route L18 and a discharge portion L19 which discharges the liquid inside the reception member 18.

Then, when the disinfecting is not performed (when not mixing the disinfecting solution with the dilution water), the pressurizing pump 15 is stopped and the back pressure valve 16 is turned off, thereby blocking the disinfecting solution inside the containing device 14 not to reach the pipe L20. The electromagnetic valve 17 is turned on, thereby controlling the flow route between the back pressure valve 16 and the pressurizing pump 15 in the pipe L17 to have the pressure lower than that of the flow route inside the pipe L20. In this manner, for example, even when a failure occurs in the back pressure valve 16 and the flow route cannot be sufficiently turned off, the disinfecting solution inside the containing device 14 is discharged outward from the discharge flow route L18. Therefore, it is possible to reliably prevent the disinfecting solution from being diffused to the dilution water inside the pipe L20.

In addition, during the disinfecting (when mixing the disinfecting solution with the dilution water), the pressurizing pump 15 is operated, the back pressure valve 16 is turned on, and the electromagnetic valve 17 is turned off, thereby controlling the flow route between the back pressure valve 16 and the pressurizing pump 15 in the pipe L17 to have the higher pressure than the flow route inside the pipe L20. In this manner, it is possible to perform the pressure injection of the disinfecting solution inside the containing device 14 on the pipe L20 through the pipe L17. Therefore, the disinfecting solution diluted by the dilution water is circulated in the pipe inside the dissolving device 3 to perform the disinfecting.

In particular, the electromagnetic valve 17 as the switching valve according to the present embodiment can be normally turned on and can be turned off using the electric conduction at optional times. That is, in the present embodiment, when mixing the disinfecting solution with the dilution water, the electric conduction is performed on the electromagnetic valve 17 and the pressurizing pump 15, and when not mixing the disinfecting solution with the dilution water, the electric conduction to the electromagnetic valve 17 and the pressurizing pump 15 is stopped.

In this manner, when mixing the disinfecting solution with the dilution water, the electric conduction is performed on the electromagnetic valve 17 and the pressurizing pump 15, and when not mixing the disinfecting solution with the dilution water, the electric conduction to the electromagnetic valve 17 and the pressurizing pump 15 is stopped. Therefore, it is possible to stop the power supply to the electromagnetic valve 17 and the pressurizing pump 15 when not mixing the disinfecting solution with the dilution water, thereby enabling running cost to be saved, in addition, when the power supply to the electromagnetic valve 17 and the pressurizing pump 15 is inadvertently stopped due to a power failure or the like, the disinfecting solution is not in a mixed state with the diluted water (the pressurizing pump 15 is stopped and the flow route between the back pressure valve 16 and the pressurizing pump 15 in the pipe L17 has the lower pressure than the pipe L20). Therefore, it is possible to improve safety.

In the present embodiment, the pressure control unit employs the electromagnetic valve 17 which can turn on and off the flow route (discharge flow route L18) using the electric conduction at optional times, but may be formed from a switching valve connected to the discharge flow route L18 whose tip is exposed to the air. Instead of the electromagnetic valve 17, a relief valve which can optionally set a relief pressure may be employed. In this manner, if the switching valve consists of the electromagnetic valve which can turn on and off the flow route at optional times or the relief valve which can optionally set the relief pressure, the pressure control unit can be more simply configured.

In addition, in the further downstream side than the connecting portion P1 with the pipe L17 in the pipe L20 according to the present embodiment, a conductivity sensor 19 (auxiliary liquid detection device) which can detect the disinfecting solution is arranged. That is, the conductivity sensor 1 can detect whether or not the disinfecting solution is mixed into the liquid by detecting the conductivity of the liquid flowing in the pipe L20. In this manner, when mixing the disinfecting solution with the dilution water, it is possible to detect that the disinfecting solution is normally injected thereto. When not mixing the disinfecting solution with the dilution water, it is possible to detect that the disinfecting solution reaches the pipe L20 due to a failure in the back pressure valve 16 (switching device) and the electromagnetic valve 17 (pressure control unit), thereby enabling the safety to be further improved. Instead of the conductivity sensor 19, another type auxiliary liquid detection device which can detect the disinfecting solution may be used.

Furthermore, in the present embodiment, after mixing the disinfecting solution with the dilution water (that is, after the disinfecting process), the electromagnetic valve 17 is turned on, the flow route between the back pressure valve 16 and the pressurizing pump 15 in the pipe L17 is controlled to have the pressure lower than that of the flow route inside the pipe L20, and the pressurizing pump 15 is operated. In this configuration, the conductivity sensor 19 (auxiliary liquid detection device) can determine whether or not the disinfecting solution is detected. In this manner, the pressure control unit can perform a self-diagnosis (self-diagnosis for checking whether or not a defect such as a malfunction has occurred in the electromagnetic valve 17), thereby enabling reliability of the device to be further improved.

According to the first embodiment, the mixing apparatus consists of the flow route branched from between the back pressure valve 16 and the pressurizing pump 15 in the pipe L17, and includes the discharge flow route L18 which can discharge the dilution water or the disinfecting solution and the electromagnetic valve 17 (pressure control unit) which can control the flow route between the back pressure valve 16 and the pressurizing pump 15 in the pipe L17 to have the pressure lower than that of the pipe L20 when not mixing the disinfecting solution with the dilution water. Therefore, even when a failure occurs in the back pressure valve 16, it is possible to reliably prevent the disinfecting solution from being unintentionally mixed into the pipe L20. In addition, according to the present embodiment, even when the pressurizing pump 15 malfunctions due to a failure, it is possible to discharge the disinfecting solution outward via the discharge flow route L18. Accordingly, it is possible to prevent the back pressure valve 16 or the pipe L17 from being damaged.

Further, the electromagnetic valve 17 as the pressure control unit according to the present embodiment can control the flow route between the back pressure valve 16 and the pressurizing pump 15 in the pipe L17 to have the high pressure than the flow route inside the pipe L20 when mixing the disinfecting solution with the dilution water. Therefore, it is possible to reliably and smoothly inject the disinfecting solution to the pipe L20, and it is possible to excellently mix the disinfecting solution with the dilution water. Furthermore, the pressure control unit according to the present embodiment consists of the electromagnetic valve 17 (switching valve) connected to the discharge flow route L18 whose tip is exposed to the air. Therefore, the pressure control unit can be simply configured. Accordingly, even when a failure occurs in the electromagnetic valve 17, it is possible to more reliably prevent the disinfecting solution from being unintentionally mixed into the pipe L20, and even when the pressurizing pump 15 malfunctions due to a failure, it is possible to more reliably prevent the back pressure valve 16 or the pipe L17 from being damaged.

In addition, the switching device according to the present embodiment consists of the back pressure valve 16 for the check valve) connected to the pipe L17, allows the liquid circulation toward the pipe L20, and regulates the liquid circulation toward the opposite direction thereof. Therefore, it is not necessary to perform the electric conduction on the back pressure valve 16 (or the check valve). Accordingly, it is possible to eliminate a need to operate the back pressure valve 16 (or the check valve) in switching between when mixing the auxiliary liquid with the main liquid and when not mixing the auxiliary liquid with the main liquid.

Figure 5:
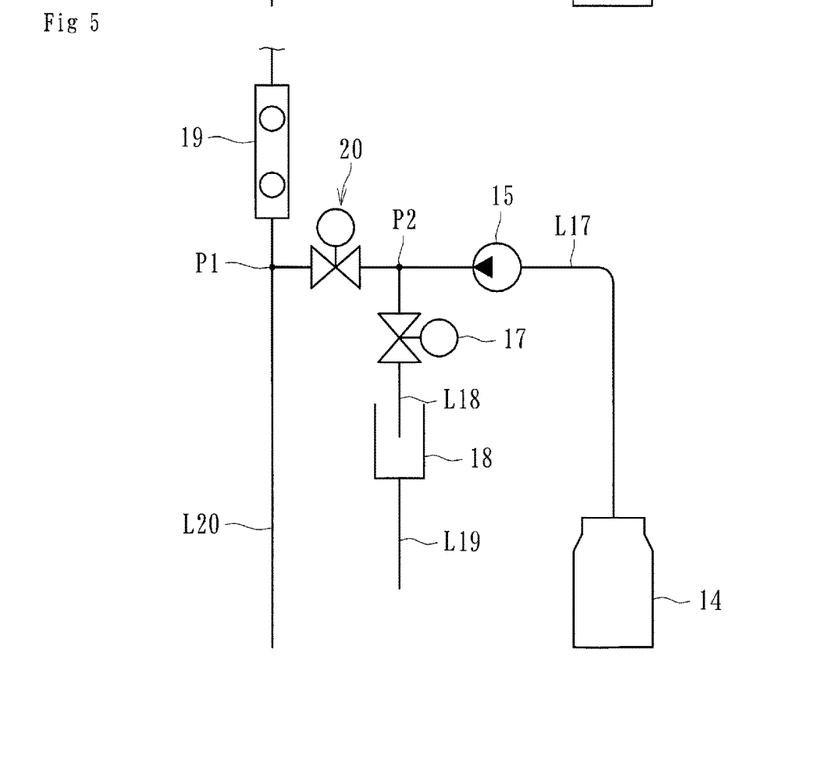
FIG. 5 is a schematic view illustrating a mixing apparatus according to another embodiment of the present disclosure.

The switching device according to the present embodiment consists of the back pressure valve 16 (or the check valve) connected to the pipe L17. However, alternatively, as illustrated in FIG. 5, an electromagnetic valve 20 which can turn on and off the flow route (pipe L17) using the electric conduction at optional times may be used. According to the electromagnetic valve 20, the electric conduction allows the electromagnetic valve 20 to be turned on and off. Therefore, it is possible to turn on and off the pipe L17 at desired times.

Figure 6:
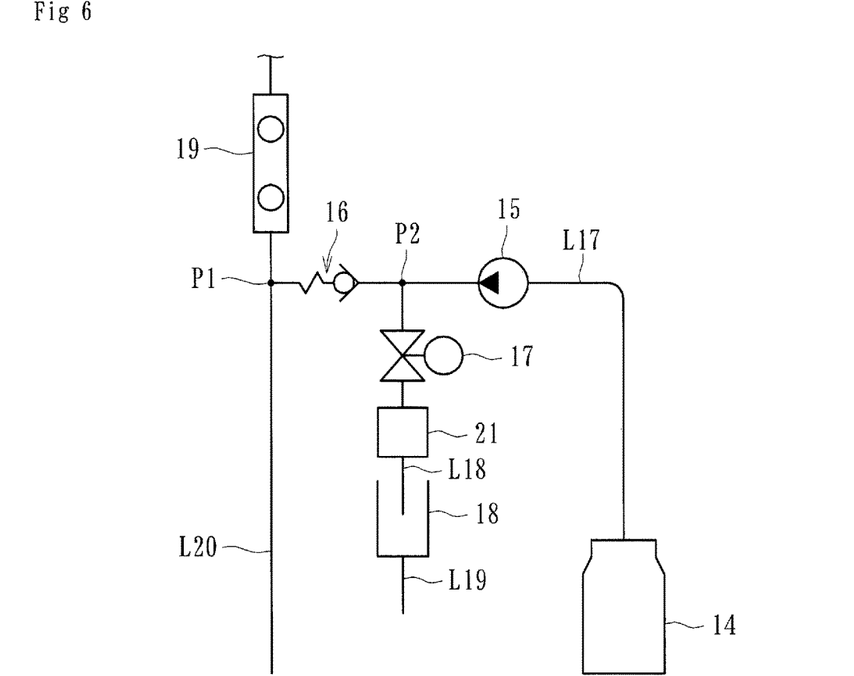
FIG. 6 is a schematic view illustrating a mixing apparatus according to still another embodiment of the present disclosure.

In addition, as illustrated in FIG. 6, in the further downstream side than the electromagnetic valve 17 in the pipe L18, a conductivity sensor 21 (main liquid detection device) which can detect the disinfecting solution may be arranged. Instead of the conductivity sensor 21, another type main liquid detection device which can detect the dilution water may be used. In this manner, the conductivity sensor 21 which detects the dilution water is arranged in the discharge flow route L18. Therefore, when not mixing the disinfecting solution with the dilution water, it is possible to detect that the dilution water leaks into the discharge flow route L18 due to a failure in the back pressure valve 16 (similar to the other switching device such as the electromagnetic valve 20).

Instead of the conductivity sensor 21, or together with the conductivity sensor 21, a liquid flow rate detection device which detects a liquid flow rate may be arranged. In this manner, if the liquid flow rate detection device which detects the liquid flow rate is arranged in the discharge flow route L18, it is possible to detect that the dilution water or the disinfecting solution unintentionally flows in the discharge flow route L18 due to a failure in the back pressure valve 16 (similar to the other switching device such as the electromagnetic valve 20) or the pressurizing pump 15.

Figure 7:
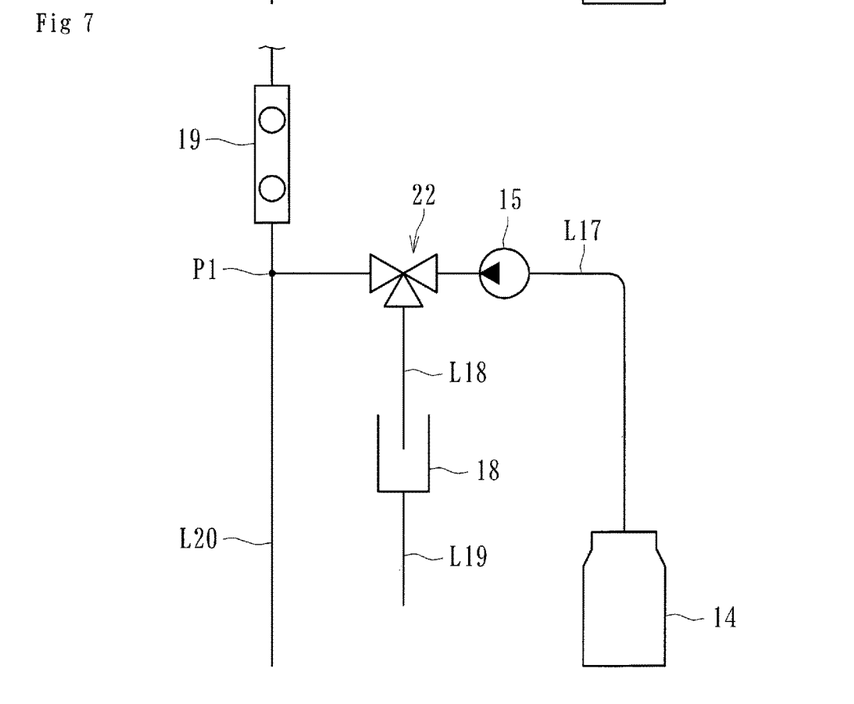
FIG. 7 is an enlarged schematic view illustrating a mixing apparatus according to a second embodiment of the present disclosure.

Next, a second embodiment according to the present disclosure will be described. Similar to the first embodiment, a mixing apparatus according to the present embodiment is applied to the dissolving device 3 configuring the blood purification system, and can perform the disinfecting by performing the pressure injection of the disinfecting solution inside the containing device 14 on the dilution water (clean water supplied from the water treatment device 4) flowing in the pipe L20 and by circulating the disinfecting solution diluted to have the predetermined concentration in the pipes of the dissolving device 3. The same reference numerals are given to configuring elements the same as those of the first embodiment, and the description thereof will not be repeated.

As illustrated in FIG. 7, the switching device and the pressure control unit according to the present embodiment consists of a three-way valve 22 arranged in a branch portion with the discharge flow route L18 in the pipe L17 (auxiliary flow route). When mixing the disinfecting solution (auxiliary liquid) with the dilution water (main liquid), the flow route from the pressurizing pump 15 in the pipe L17 toward the pipe L20 (main unit) is turned on and the flow route toward the discharge flow route L18 is turned off, and when not mixing the disinfecting solution with the dilution water, the flow route from the pressurizing pump 15 in the pipe L17 toward the pipe L20 is turned off and the flow route toward the discharge flow route L18 is turned on. That is, in the present embodiment, the three-way valve 22 is configured to serve as both the switching device and the pressure control unit.

More specifically, the three-way valve 22 according to the present embodiment consists of a three-way electromagnetic valve which normally (during no electric conduction) turns on the flow route from the pressurizing pump 15 in the pipe L17 toward the pipe L20 and turns off the flow route toward the discharge flow route L18, and using the electric conduction, turns off the flow route from the pressurizing pump 15 in the pipe L17 toward the pipe L20 and turns on the flow route toward the discharge flow route L18. That is, the three-way valve 22 according to the present embodiment controls both the flow route from the pressurizing pump 15 in the pipe L17 toward the pipe L20 and the flow route toward the discharge flow route L18 so as not to be turned on or off.

When mixing the disinfecting solution with the dilution water, the electric conduction is not performed on the three-way valve 22, the flow route from the pressurizing pump 15 in the pipe L17 toward the pipe L20 is turned on and the flow route toward the discharge flow route L18 is turned off. When not mixing the disinfecting solution with the dilution water, the flow route from the pressurizing pump 15 in the pipe L17 toward the pipe L20 is turned off and the flow route toward the discharge flow route L18 is turned on. According to this configuration, when not mixing the disinfecting solution with the dilution water, the flow route between the three-way valve 22 and the pressurizing pump 15 in the pipe L17 can be controlled to have the pressure lower than that of the pipe L20, and when mixing the disinfecting solution with the dilution water, the flow route between the back pressure valve 16 and the pressurizing pump 15 in the pipe L17 can be controlled to have the higher pressure than the pipe L20.

According to the second embodiment, the switching device and the pressure control unit are formed from the three-way valve 22 arranged in the branch portion with the discharge flow route L18 in the pipe L17. When mixing the disinfecting solution with the dilution water, the flow route from the pressurizing pump 15 in the pipe L17 toward the pipe L20 is turned on and the flow route toward the discharge flow route L18 is turned off. When not mixing the disinfecting solution with the dilution water, the flow route from the pressurizing pump 15 in the pipe L17 toward the pipe L20 is turned off and the flow route toward the discharge flow route L18 is turned on. Therefore, as compared to a case of forming the switching device and the pressure control unit respectively, it is possible to reduce the number of parts. Further, since one signal can lead to the operation, it is possible to more easily perform the switching operation during the switching between when mixing the disinfecting solution with the dilution water and when not mixing the disinfecting solution with the dilution water.

In addition, according to the present embodiment, similar to the first embodiment, there are provided the discharge flow route L18 which consists of the flow route branched from the three-way valve 22 in the pipe L17 and can discharge the dilution water or the disinfecting solution, and the three-way valve 22 (pressure control unit) which can control the flow route between the three-way valve 22 and the pressurizing pump 15 in the pipe L17 to have the pressure lower than that of the pipe L20 when not mixing the disinfecting solution with the dilution water. Therefore, it is possible to reliably prevent the disinfecting solution from being unintentionally mixed into the pipe L20. Furthermore, the three-way valve 22 as the pressure control unit according to the present embodiment can control the flow route between the back pressure valve 16 and the pressurizing pump 15 in the pipe L17 to have the higher pressure than the pipe L20 when mixing the disinfecting solution with the dilution water. Therefore, it is possible to reliably and smoothly inject the disinfecting solution to the pipe L20, and it is possible to excellently mix the disinfecting solution with the dilution water.

According to the first embodiment and the second embodiment, the auxiliary liquid is formed of the disinfecting solution for disinfecting the main unit. Therefore, it is possible to more smoothly mix the disinfecting solution with the main liquid (dilution water) during the disinfecting, and it is possible to more reliably prevent the disinfecting solution from being mixed into the main liquid when the disinfecting is not performed.

Figure 8:
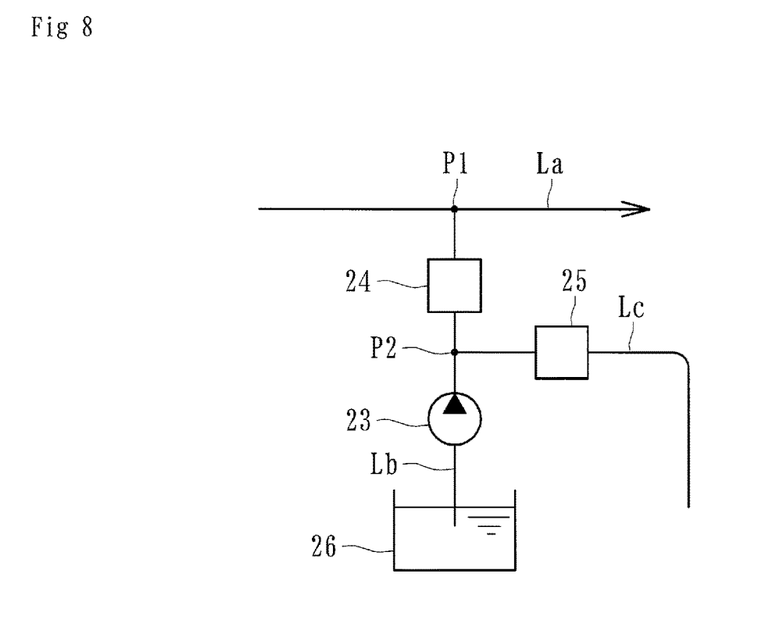
FIG. 8 is a conceptual diagram illustrating the mixing apparatus of the present disclosure.

Hitherto, the present embodiments have been described, but the present disclosure is not limited thereto. As illustrated in FIG. 8, the mixing apparatus may include a main flow route La (main unit); an auxiliary flow route Lb which circulates the auxiliary liquid and whose tip is connected to the main flow route La; a pressurizing device 23 which circulates the auxiliary liquid in the auxiliary flow route toward the main flow route La; and a switching device 24 which is arranged near a connecting portion P1 with the main flow route La in the auxiliary flow route Lb and which can optionally turn on and off the auxiliary flow route Lb. When mixing the auxiliary liquid with the main liquid, the switching device 24 is turned on and the pressurizing device 23 is operated, thereby performing the pressure injection of the auxiliary liquid on the main flow route La through the auxiliary flow route Lb. When not mixing the auxiliary liquid with the main liquid, the switching device 24 is turned off and the pressurizing device 23 is stopped. It is sufficient as long as the mixing apparatus include a discharge flow route Lc which consists of a flow route branched from between the switching device 24 and the pressurizing device 23 in the auxiliary flow route Lb, and which can discharge the main liquid or the auxiliary liquid, and a pressure control unit 25 which can control the flow route between the switching device 24 and the pressurizing device 23 in the auxiliary flow route Lb to have a pressure lower than that of the main flow route La when not mixing the auxiliary liquid with the main liquid.

Then, it is sufficient as long as the pressure control unit 25 can control the flow route between the switching device 24 and the pressurizing device 23 in the auxiliary flow route Lb to have a higher pressure than the main flow route La when mixing the auxiliary liquid with the main liquid. Instead of those formed from the switching valve as described above in the embodiment, for example, those formed from a chamber connected to a discharge flow route Lc and a pressure adjustment unit which can increase or decrease a pressure (hydraulic pressure or atmospheric pressure) inside the chamber may be used. Furthermore, the pressure control unit according to the present embodiment controls the flow route between the switching device 24 and the pressurizing device 23 in the auxiliary flow route Lb to have the higher pressure than the main flow route La when mixing the auxiliary liquid with the main liquid. However, the pressure control unit may include those which control a pressure in the flow route between the switching device 24 and the pressurizing device 23 in the auxiliary flow route Lb to be equal to a pressure the main flow route La (that is, those which can control the pressure in the flow route between the switching device 24 and the pressurizing device 23 in the auxiliary flow route Lb to be equal to or higher than the pressure the main flow route La (including a containing device 26 to be described)).

Figure 9:
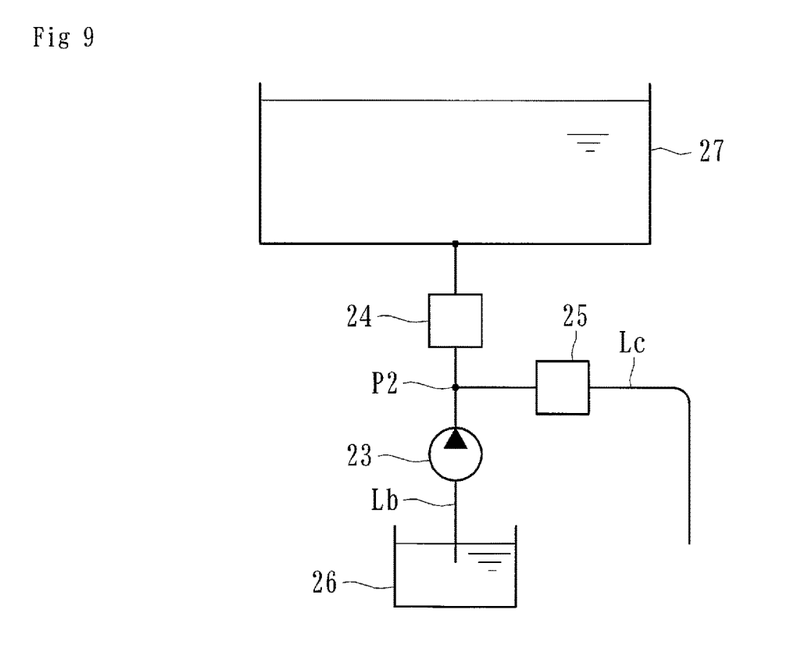
FIG. 9 is a conceptual diagram illustrating that the mixing apparatus according to the present disclosure is applied to another form.

In addition, instead of the pressurizing pump 15 as described above in the embodiment, the pressurizing device 23 may be a syringe which can perform the pressure injection of the auxiliary liquid on the main unit. Further, in the present disclosure, instead of the main flow route La (main unit) circulating the main liquid, as illustrated in FIG. 9, a main unit 27 containing the main liquid may be adopted. The reference numeral 26 in FIGS. 8 and 9 indicates a containing device which can contain a predetermined amount of the auxiliary liquid.

Furthermore, in the present embodiments, both of the mixing apparatus are applied to the dissolving device 3 configuring the blood purification system, but may be applied to other devices (monitoring device 1, dialysate supplying device 2 or water treatment device 4) configuring the blood purification system. According to the present disclosure, the main unit consists of a flow route for circulating the dialysate for purifying the blood of the patient, the undiluted dialysate and the clean water for producing the dialysate or the undiluted dialysate, and the main liquid is formed of the dilution water for producing the disinfecting solution having the predetermined concentration by diluting the disinfecting solution. Therefore, it is possible to more smoothly mix the disinfecting solution with the dilution water during the disinfecting, and it is possible to more reliably prevent the disinfecting solution from being mixed into the dialysate, the undiluted dialysate and the clean water for the dialysate or the undiluted dialysate when the disinfecting is not performed. The present disclosure may be applied to a blood purification system including a personal dialysis device having a blood purifier (dialyzer) and various devices capable of supplying the water and the undiluted dialysate to the personal dialysis device.

In addition, the present disclosure is not limitedly applied to various devices configuring the blood purification system, but for example, may be widely applied to other devices (for example, a manufacturing apparatus or a plant for manufacturing industrial products or parts) which needs the switching operation between when mixing the auxiliary liquid with the main liquid and when not mixing the auxiliary liquid with the main liquid. Of course, in this case, various liquids can be used if the main liquid and the auxiliary liquid are formed of two different liquids.

A mixing apparatus can be applied to those which have other added functions if the mixing apparatus includes a discharge flow route which consists of a flow route branched from between a switching device and a pressurizing device in an auxiliary flow route and which can discharge a main liquid or an auxiliary liquid: and a pressure control unit which can control the flow route between the switching device and the pressurizing device in the auxiliary flow route to have a pressure lower than that of a main unit when not mixing the auxiliary liquid with the main liquid.

REFERENCE LIST

1. monitoring device
2 dialysate supplying device
3 dissolving device
4 water treatment device
5 dialyzer
6 blood circuit
7 duplex pump
8 containing device
9 containing device
10 dissolving tank
11 storage tank
12 dissolving tank
13 storage tank
14 containing device
15 pressurizing pump (pressurizing device)
16 back pressure valve (switching device)
17 electromagnetic valve (switching valve)
18 reception unit
19 conductivity sensor (auxiliary liquid detection device)
20 electromagnetic valve (switching device)
21 conductivity sensor (main liquid detection device)
22 three-way valve
23 pressurizing device
24 switching device
25 pressure control unit
L17 pipe (auxiliary flow route)
L18 discharge flow route
L20 pipe (main unit)

We claim:
1. A mixing apparatus for a blood purification system comprising:

a main unit that circulates a main liquid through a main flow route or contains the main liquid in a containing device;
an auxiliary flow route that circulates an auxiliary liquid and whose tip is connected to the main unit;
a containing device in the auxiliary flow route;
a pressurizing device that is arranged along a portion in the auxiliary flow route that circulates the auxiliary liquid in the auxiliary flow route toward the main unit; and
a switching device that is arranged along a portion in the auxiliary flow route between the tip connected to the main unit and the pressurizing device, and that optionally turns on and off the auxiliary flow route,
wherein the main flow route or the containing device include a dialysate for purifying blood of a patient, an undiluted dialysate, or clean water for producing the dialysate or the undiluted dialysate;
wherein the auxiliary liquid is a disinfecting solution that disinfects the main unit;
wherein the containing device includes the disinfecting solution;
wherein when mixing the auxiliary liquid with the main liquid, pressure injection of the auxiliary liquid is performed on the main unit through the auxiliary flow route by turning on the switching device and operating the pressurizing device, and when not mixing the auxiliary liquid with the main liquid, the switching device is turned off and the pressurizing device is stopped, and
wherein the mixing apparatus further comprises:
a discharge flow route including a branched flow route having a connection end and a discharge end;
a pressure control unit located along the discharge flow route, the pressure control unit controls a flow route segment of the auxiliary flow route located between the switching device and the pressurizing device in the auxiliary flow route;
wherein the connection end of the discharge flow route is directly branched from the flow route segment and the branched flow route extends away from the auxiliary flow route to the discharge end so that the main liquid is discharged from the main flow route and the auxiliary liquid is discharged from the auxiliary flow route to a location outside of the auxiliary flow route and the main flow route; and
wherein the pressure control unit controls the auxiliary flow route segment between the switching device and the pressurizing device, so that the auxiliary flow route has a pressure lower than that of the main unit, when not mixing the auxiliary liquid with the main liquid.

2. The mixing apparatus according to claim 1, wherein when mixing the auxiliary liquid with the main liquid, the pressure control unit controls the auxiliary flow route segment between the switching device and the pressurizing device, so that the auxiliary flow route has a pressure equal to or greater than a pressure of the main unit.

3. The mixing apparatus according to claim 2, wherein the switching device consists of a back pressure valve connected to the auxiliary flow route or a check valve, allows liquid circulation toward the main unit, and regulates the liquid circulation toward an opposite direction thereof.

4. The mixing apparatus according to claim 1, wherein the pressure control unit consists of a switching valve which is connected to the discharge flow route and a tip of the discharge end is exposed to air.

5. The mixing apparatus according to claim 4, wherein the switching valve consists of an electromagnetic valve which turns on and off the discharge flow route at optional times or a relief valve which optionally sets a relief pressure.

6. The mixing apparatus according to claim 4, wherein the switching valve consists of an electromagnetic valve which is normally turned on and is turned off by way of electric conduction at optional times, and
wherein when mixing the auxiliary liquid with the main liquid, the electric conduction is performed on the electromagnetic valve and the pressurizing device, and when not mixing the auxiliary liquid with the main liquid, the electric conduction to the electromagnetic valve and the pressurizing device is stopped.

7. The mixing apparatus according to claim 1, wherein the switching device consists of a back pressure valve connected to the auxiliary flow route or a check valve, allows liquid circulation toward the main unit, and regulates the liquid circulation toward an opposite direction thereof.

8. The mixing apparatus according to claim 1, wherein a main liquid detection device which detects the main liquid is arranged in the discharge flow route.

9. The mixing apparatus according to claim 1, wherein a liquid flow rate detection device which detects a liquid flow rate is arranged in the discharge flow route.

10. The mixing apparatus according to claim 1, wherein an auxiliary liquid detection device which detects the auxiliary liquid is arranged in the main unit, and
wherein the auxiliary liquid detection device detects the auxiliary liquid during mixing of the auxiliary liquid with the main liquid and detects any auxiliary liquid in the main unit due to the failure in the switching device and the pressurizing device when the auxiliary liquid is not mixing with the main liquid.

11. The mixing apparatus according to claim 10, wherein after mixing the auxiliary liquid with the main liquid, the pressure control unit controls the auxiliary flow route segment between the switching device and the pressurizing device, so that the auxiliary flow route has a pressure lower than that of the main unit and operates the pressurizing device so that the auxiliary liquid detection device can determine whether or not the auxiliary liquid is detected.

12. The mixing apparatus according to claim 10
wherein the switching device consists of a back pressure valve connected to the auxiliary flow route or a check valve, allows liquid circulation toward the main unit, and regulates the liquid circulation toward an opposite direction thereof.

13. A mixing apparatus comprising:
a main unit including a main unit flow route that circulates or contains a main liquid;
an auxiliary flow route that circulates an auxiliary liquid and whose tip is connected to the main unit flow route;
a discharge flow route including a discharge end and a connection end, the connection end is directly branched from a segment of the auxiliary flow route between a switching device in the auxiliary flow route and a pressurizing device in the auxiliary flow route;
the pressurizing device located along the auxiliary flow route circulates the auxiliary liquid in the auxiliary flow route toward the main unit flow route;
the switching device is located along the auxiliary flow route between the pressurizing device and a connecting portion of the auxiliary flow route and the main unit flow route, the switching device optionally turns on and off the auxiliary flow route;

a pressure control unit located along the discharge flow route, the pressure control unit controls the segment of the auxiliary flow route, so that the auxiliary flow route has a pressure lower than that of the main unit flow route when not mixing the auxiliary liquid with the main liquid; and an auxiliary liquid detection device located along the main unit flow route and downstream of the connecting portion of the auxiliary flow route and the main unit flow route, the auxiliary liquid detection device detects the auxiliary liquid in the main unit flow route due to a failure of the switching device and the pressure control unit; and wherein the switching device turns on the auxiliary flow route when mixing the auxiliary liquid with the main liquid and pressure injection of the auxiliary liquid is performed on the main unit flow route through the auxiliary flow route by operation of the pressurizing device;

wherein the switching device turns off the auxiliary flow route when not mixing the auxiliary liquid with the main liquid so that the pressurizing device is stopped;

wherein the pressure control unit prevents the auxiliary liquid from being unintentionally mixed into the main unit flow route due to a failure of the switching device; and wherein the pressure control unit prevents damage to the switching device and auxiliary flow route due to a failure of the pressurizing pump by discharging the auxiliary liquid through the discharge route.

14. The mixing apparatus according to claim 13,
wherein the main unit flow route is fluidly connected to a device of a blood purification apparatus selected from a monitoring device, a dialysate supplying device, and a dissolving device;
wherein the auxiliary liquid is a disinfecting solution and a base end of the auxiliary flow route connects to a containing device containing the disinfecting solution; and
wherein the pressure injected auxiliary liquid is mixed with the main unit liquid and mixes to produce a disinfecting solution with a predetermined concentration which circulates through the main unit flow route to the fluidly connected device.

15. The mixing apparatus according to claim 13,
wherein the pressurizing device is a diaphragm pump;
wherein the switching device is a back pressure valve;
wherein the pressure control unit is an electromagnetic valve; and
wherein the auxiliary liquid detection device is a conductivity sensor.

* * * * *